US009174913B2

(12) United States Patent
Johnson et al.

(10) Patent No.: US 9,174,913 B2
(45) Date of Patent: Nov. 3, 2015

(54) PROCESS FOR THE PRODUCTION OF METHACRYLIC ACID AND ITS DERIVATIVES AND POLYMERS PRODUCED THEREFROM

(75) Inventors: David William Johnson, Wilton Redcar (GB); Graham Ronald Eastham, Wilton Redcar (GB); Martyn Poliakoff, Nottingham (GB); Thomas Andrew Huddle, Guildford (GB)

(73) Assignee: Lucite International UK Limited, Southampton (GB)

( * ) Notice: Subject to any disclaimer, the term of this patent is extended or adjusted under 35 U.S.C. 154(b) by 0 days.

(21) Appl. No.: 13/989,363

(22) PCT Filed: Nov. 18, 2011

(86) PCT No.: PCT/GB2011/052271
§ 371 (c)(1),
(2), (4) Date: Jun. 25, 2013

(87) PCT Pub. No.: WO2012/069813
PCT Pub. Date: May 31, 2012

(65) Prior Publication Data
US 2013/0303713 A1    Nov. 14, 2013

(30) Foreign Application Priority Data

Nov. 24, 2010   (GB) .................................. 1019915.6
Mar. 31, 2011   (GB) .................................. 1105467.3

(51) Int. Cl.
*C07B 37/06*      (2006.01)
*C07C 51/38*      (2006.01)
(Continued)

(52) U.S. Cl.
CPC ................. *C07C 51/38* (2013.01); *C07C 67/00* (2013.01); *C08F 20/06* (2013.01); *C08F 20/10* (2013.01); *C08F 20/14* (2013.01)

(58) Field of Classification Search
CPC ........ C07C 57/04; C07C 51/38; C07C 45/676
USPC .................................................. 562/598, 599
See application file for complete search history.

(56) References Cited

U.S. PATENT DOCUMENTS 2,504,049 A    4/1950    Richards
3,962,074 A    6/1976    Schropp
(Continued)

FOREIGN PATENT DOCUMENTS

BE       550 710 A        12/1959
CN       101497563 A       8/2009
(Continued)

OTHER PUBLICATIONS

Office Action issued in Chinese Patent Application No. 201180056814.1 dated May 27, 2014.
(Continued)

*Primary Examiner* — Vu A Nguyen
(74) *Attorney, Agent, or Firm* — Venable LLP; Keith G. Haddaway; Annette K. Kwok (57) ABSTRACT

A process for the production of methacrylic acid is described. The process comprises the base catalysed decarboxylation of at least one or a mixture of dicarboxylic acids selected from itaconic, citraconic or mesaconic acid. The decarboxylation is carried out in the range greater than 240 and up to 275° C. to provide high selectivity. The methacrylic acid product may be esterified to produce an ester. A method of preparing polymers or copolymers of methacrylic acid or methacrylic acid esters using the process is also described. Optionally, the process may be preceded with a decarboxylation and, if necessary, a dehydration step on a source of pre-acid such as citric acid or isocitric acid.

13 Claims, 1 Drawing Sheet

(51) Int. Cl.
  *C07C 67/00* (2006.01)
  *C08F 20/06* (2006.01)
  *C08F 20/10* (2006.01)
  *C08F 20/14* (2006.01)

(56) References Cited

U.S. PATENT DOCUMENTS

| | | |
|---|---|---|
| 4,555,557 A | 11/1985 | Fukumoto et al. |
| 5,612,417 A | 3/1997 | Rhein et al. |
| 2005/0085607 A1 | 4/2005 | Kabs et al. |
| 2010/0273970 A1 | 10/2010 | Koestner et al. |
| 2011/0287991 A1 | 11/2011 | Dubois |
| 2012/0309911 A1 | 12/2012 | Johnson et al. |

FOREIGN PATENT DOCUMENTS

| | | |
|---|---|---|
| EP | 0 716 122 A2 | 6/1996 |
| JP | H08-208917 A | 8/1996 |
| JP | 2005-516089 A | 6/2005 |
| WO | WO-2010/058119 A1 | 5/2010 |
| WO | WO-2011/077140 A2 | 6/2011 |

OTHER PUBLICATIONS

International Preliminary Report on Patentability and Written Opinion in PCT International Application No. PCT/GB2011/052271, dated May 28, 2013.
Communication pursuant to Rules 161(1) and 162 EPC in European Patent Application No. 11791623.9-1451, dated Jul. 2, 2013.
Li et al., "Spectroscopy of Hydrothermal Solutions 18: pH-Dependent Kinetics of Itaconic Acid Reactions in Real Time", Journal of Physical Chemistry, vol. 105, pp. 10839-10845, 2001.
Salov et al., "High-temperature conversions of alkyl-substituted acrylic acids in aqueous solutions", Zhurnal Organicheskoi Khimii, vol. 19, No. 10, pp. 2052-2054, 1983.
Search Report in Application No. GB1019915.6 dated May 18, 2011.
Carlsson et al., "Study of the sequential conversion of citric to itaconic to methacrylic acid in near-critical and supercritical water," Industrial & Engineering Chemistry Research, American Chemical Society, vol. 33, No. 8, pp. 1989-1996 (1994).
International Search Report in PCT International Application No. PCT/GB2011/052271 dated Feb. 7, 2012.
Restriction Requirement issued in U.S. Appl. No. 13/984,473 dated Nov. 25, 2014.
Magnus et al., "Study of the sequential conversion of citric to itaconic to methacrylic acid in near-critical and supercritical water," Industrial & Engineering Chemistry Research, American Chemical Society, vol. 33, No. 8, pp. 1989-1996 (1994).
International Search Report in PCT International Application No. PCT/GB2012/050272 dated May 7, 2012.
International Preliminary Report on Patentability issued in International Application No. PCT/GB2012/050272 dated Aug. 13, 2013.
Office Action issued in New Zealand Patent Application No. 613224 dated May 5, 2014.
Notice of Allowance issued in U.S. Appl. No. 13/984,473 dated Mar. 13, 2015.

Schematic of apparatus used for experiments.

PROCESS FOR THE PRODUCTION OF METHACRYLIC ACID AND ITS DERIVATIVES AND POLYMERS PRODUCED THEREFROM

The present invention relates to a process for the production of methacrylic acid or derivatives such as esters thereof by the decarboxylation of itaconic acid or a source thereof in the presence of base catalysts, in particular, but not exclusively, a process for the production of methacrylic acid or methyl methacrylate.

Methacrylic acid and its methyl ester, methyl methacrylate (MMA) are important monomers in the chemical industry. Their main application is in the production of plastics for various applications. The most significant polymerisation application is the casting, moulding or extrusion of polymethyl methacrylate (PMMA) to produce high optical clarity plastics. In addition, many copolymers are used, important copolymers are copolymers of methyl methacrylate with α-methyl styrene, ethyl acrylate and butyl acrylate. Currently MMA (and MAA) is produced entirely from petrochemical feedstocks.

Conventionally, MMA has been produced industrially via the so-called acetone-cyanohydrin route. The process is capital intensive and produces MMA from acetone and hydrogen cyanide at a relatively high cost. The process is effected by forming acetone cyanohydrin from the acetone and hydrogen cyanide: dehydration of this intermediate yields methacrylamide sulphate, which is then hydrolysed to produce MAA. The intermediate cyanohydrin is converted with sulphuric acid to a sulphate ester of the methacrylamide, methanolysis of which gives ammonium bisulphate and MMA. However, this method is not only expensive, but both sulphuric acid and hydrogen cyanide require careful and expensive handling to maintain a safe operation and the process produces large amounts of ammonium sulphate as a by-product. Conversion of this ammonium sulphate either to a useable fertilizer or back to sulphuric acid requires high capital cost equipment and significant energy costs.

Alternatively, in a further process, it is known to start with an isobutylene or, equivalently, t-butanol reactant which is then oxidized to methacrolein and then to MAA.

An improved process that gives a high yield and selectivity and far fewer by-products is a two stage process known as the Alpha process. Stage I is described in WO96/19434 and relates to the use of 1,2-bis-(di-t-butylphosphinomethyl)benzene ligand in the palladium catalysed carbonylation of ethylene to methyl propionate in high yield and selectivity. The applicant has also developed a process for the catalytic conversion of methyl propionate (MEP) to MMA using formaldehyde. A suitable catalyst for this is a caesium catalyst on a support, for instance, silica. This two stage process although significantly advantageous over the competitive processes available still nevertheless relies on ethylene feed stocks predominantly from crude oil and natural gas, albeit bioethanol is also available as a source of ethylene.

For many years, biomass has been offered as an alternative to fossil fuels both as a potential alternative energy resource and as an alternative resource for chemical process feedstocks. Accordingly, one obvious solution to the reliance on fossil fuels is to carry out any of the known processes for the production of MMA or MAA using a biomass derived feedstock.

In this regard, it is well known that syngas (carbon monoxide and hydrogen) can be derived from Biomass and that methanol can be made from syngas. Several Industrial plants produce methanol from syngas on this basis, for example, at Lausitzer Analytik GmbH Laboratorium für Umwelt and Brennstoffe Schwarze Pumpe in Germany and Biomethanol Chemie Holdings, Delfzijl, Netherlands. Nouri and Tillman, Evaluating synthesis gas based biomass to plastics (BTP) technologies, (ESA-Report 2005:8 ISSN 1404-8167) teach the viability of using methanol produced from synthesis gas as a direct feedstock or for the production of other feedstocks such as formaldehyde. There are also many patent and non-patent publications on production of syngas suitable for production of chemicals from biomass.

The production of ethylene by dehydration of biomass derived ethanol is also well established with manufacturing plants in, especially, Brazil.

The production of propionic acid from carbonylation of ethanol and the conversion of biomass derived glycerol to molecules such as acrolein and acrylic acid is also well established in the patent literature.

Thus ethylene, carbon monoxide and methanol have well established manufacturing routes from biomass. The chemicals produced by this process are either sold to the same specification as oil/gas derived materials, or are used in processes where the same purity is required.

Thus in principle there is no barrier to operation of the so called Alpha process above to produce methyl propionate from Biomass derived feedstocks. In fact, its use of simple feedstocks such as ethylene, carbon monoxide and methanol rather sets it apart as an ideal candidate.

In this regard, WO2010/058119 relates explicitly to the use of biomass feedstocks for the above Alpha process and the catalytic conversion of methyl propionate (MEP) produced to MMA using formaldehyde. These MEP and formaldehyde feedstocks could come from a biomass source as mentioned above. However, such a solution still involves considerable processing and purification of the biomass resource to obtain the feedstock which processing steps themselves involve the considerable use of fossil fuels.

Further, the Alpha process requires multiple feedstocks in one location which can lead to availability issues. It would therefore be advantageous if any biochemical route avoided multiple feedstocks or lowered the number of feedstocks.

Therefore, an improved alternative non-fossil fuel based route to acrylate monomers such as MMA and MAA is still required.

PCT/GB2010/052176 discloses a process for the manufacture of aqueous solutions of acrylates and methacrylates respectively from solutions of malate and citramalate acids and their salts.

Carlsson et al., Ind. Eng. Chem. Res. 1994, 33, 1989-1996 has disclosed itaconic acid decarboxylation to MAA at high temperatures of 360° C. and with a maximum yield of 70%. Carlsson found a decrease in selectivity in moving from 360 to 350° C. under ideal conditions.

Generally, for industrial processes a high selectivity is required to avoid generation of unwanted by-products which would eventually render a continuous process untenable. For this purpose, particularly for a continuous process, selectivity for the desired product should exceed 90%.

Surprisingly, it has now been discovered that high selectivity to MAA formation in excess of 90% in the decarboxylation of itaconic acid and other itaconic equilibrated acids can be achieved at significantly lower temperatures.

According to a first aspect of the present invention there is provided a process for the production of methacrylic acid by the base catalysed decarboxylation of at least one dicarboxylic acid selected from itaconic, citraconic or mesaconic acid or mixtures thereof, wherein the decarboxylation is carried out at a temperature in the range greater than 240 up to 275° C.

The dicarboxylic acid(s) reactants and the base catalyst need not necessarily be the only compounds present. The dicarboxylic acid(s) together with any other compounds present are generally dissolved in an aqueous solution for the base catalysed thermal decarboxylation.

Advantageously, carrying out the decarboxylation at lower temperatures prevents the production of significant amounts of by-products which may be difficult to remove and may cause further purification and processing problems in an industrial process. Therefore, the process provides a surprisingly improved selectivity in this temperature range. Furthermore, lower temperature decarboxylation uses less energy and thereby creates a smaller carbon footprint than high temperature decarboxylations.

The dicarboxylic acids are available from non-fossil fuel sources. For instance, the itaconic, citraconic or mesaconic acids could be produced from a source of pre-acids such as citric acid or isocitric acid by dehydration and decarboxylation at suitably high temperatures or from aconitic acid by decarboxylation at suitably high temperatures. It will be appreciated that a base catalyst is already present so that the source of pre-acid dehydration and/or decomposition may potentially be base catalysed under such suitable conditions. Citric acid and isocitric acid may themselves be produced from known fermentation processes and aconitic acid may be produced from the former acids. Accordingly, the process of the invention goes some way to providing a biological or substantially biological route to generate methacrylates directly whilst minimising reliance on fossil fuels.

As detailed above, the base catalysed decarboxylation of the at least one dicarboxylic acid takes place at less than 270° C., more typically, at less than 265° C., more preferably, at up to 270° C., most preferably at up to 265° C. In any case, a preferred lower temperature for the process of the present invention is 245° C., more preferably, 250° C., most preferably, 255° C. Preferred temperature ranges for the process of the present invention are between 245° C. and up to 270° C., more preferably, between 250° C. and 270° C., most preferably, between 255° C. and 265° C.

Preferably, the reaction takes place at a temperature at which the reaction medium is in the liquid phase. Typically, the reaction medium is an aqueous solution.

Preferably, the base catalysed decarboxylation takes place with the dicarboxylic acid reactants and preferably the base catalyst in aqueous solution.

To maintain the reactants in the liquid phase under the above temperature conditions the decarboxylation reaction of the at least one dicarboxylic acid is carried out at suitable pressures in excess of atmospheric pressure. Suitable pressures which will maintain the reactants in the liquid phase in the above temperature ranges are greater than 200 psi, more suitably, greater than 300 psi, most suitably, greater than 450 psi and in any case at a higher pressure than that below which the reactant medium will boil. There is no upper limit of pressure but the skilled person will operate within practical limits and within apparatus tolerances, for instance, at less than 10,000 psi, more typically, at less than 5,000 psi, most typically, at less than 4000 psi.

Preferably, the above reaction is at a pressure of between about 200 and 10000 psi. More preferably, the reaction is at a pressure of between about 300 and 5000 psi and yet more preferably between about 450 and 3000 psi.

In a preferred embodiment, the above reaction is at a pressure at which the reaction medium is in the liquid phase.

Preferably, the reaction is at a temperature and pressure at which the reaction medium is in the liquid phase.

As mentioned above, the catalyst is a base catalyst.

Preferably, the catalyst comprises a source of $OH^-$ ions. Preferably, the base catalyst comprises a metal oxide, hydroxide, carbonate, acetate (ethanoate), alkoxide, hydrogencarbonate or salt of a decomposable di- or tri-carboxylic acid, or a quaternary ammonium compound of one of the above; more preferably a Group I or Group II metal oxide, hydroxide, carbonate, acetate, alkoxide, hydrogencarbonate or salt of a di- or tri-carboxylic acid or methacrylic acid. The base catalyst may also comprise one or more amines.

Preferably, the base catalyst is selected from one or more of the following: $LiOH$, $NaOH$, $KOH$, $Mg(OH)_2$, $Ca(OH)_2$, $Ba(OH)_2$, $CsOH$, $Sr(OH)_2$, $RbOH$, $NH_4OH$, $Li_2CO_3$, $Na_2CO_3$, $K_2CO_3$, $Rb_2CO_3$, $Cs_2CO_3$, $MgCO_3$, $CaCO_3$, $SrCO_3$, $BaCO_3$, $(NH_4)_2CO_3$, $LiHCO_3$, $NaHCO_3$, $KHCO_3$, $RbHCO_3$, $CsHCO_3$, $Mg(HCO_3)_2$, $Ca(HCO_3)_2$, $Sr(HCO_3)_2$, $Ba(HCO_3)_2$, $NH_4HCO_3$, $Li_2O$, $Na_2O$, $K_2O$, $Rb_2O$, $Cs_2O$, $MgO$, $CaO$, $SrO$, $BaO$, $Li(OR^1)$, $Na(OR^1)$, $K(OR^1)$, $Rb(OR^1)$, $Cs(OR^1)$, $Mg(OR^1)_2$, $Ca(OR^1)_2$, $Sr(OR^1)_2$, $Ba(OR^1)_2$, $NH_4(OR^1)$ where $R^1$ is any $C_1$ to $C_6$ branched, unbranched or cyclic alkyl group, being optionally substituted with one or more functional groups; $NH_4(RCO_2)$, $Li(RCO_2)$, $Na(RCO_2)$, $K(RCO_2)$, $Rb(RCO_2)$, $Cs(RCO_2)$, $Mg(RCO_2)_2$, $Ca(RCO_2)_2$, $Sr(RCO_2)_2$ or $Ba(RCO_2)_2$, where $RCO_2$ is selected from citramalate, mesaconate, citraconate, itaconate, citrate, oxalate and methacrylate; $(NH_4)_2(CO_2RCO_2)$, $Li_2(CO_2RCO_2)$, $Na_2(CO_2RCO_2)$, $K_2(CO_2RCO_2)$, $Rb_2(CO_2RCO_2)$, $Cs_2(CO_2RCO_2)$, $Mg(CO_2RCO_2)$, $Ca(CO_2RCO_2)$, $Sr(CO_2RCO_2)$, $Ba(CO_2RCO_2)$, $(NH_4)_2(CO_2RCO_2)$, where $CO_2RCO_2$ is selected from citramalate, mesaconate, citraconate, itaconate and oxalate; $(NH_4)_3(CO_2R(CO2)CO_2)$, $Li_3(CO_2R(CO_2)CO_2)$, $Na_3(CO_2R(CO2)CO_2)$, $K_3(CO_2R(CO_2)CO_2)$, $Rb_3(CO_2R(CO_2)CO_2)$, $Cs_3(CO_2R(CO_2)CO_2)$, $Mg_3(CO_2R(CO_2)CO_2)_2$, $Ca_3(CO_2R(CO_2)CO_2)_2$, $Sr_3(CO_2R(CO_2)CO_2)_2$, $Ba_3(CO_2R(CO_2)CO_2)_2$, $(NH_4)_3(CO_2R(CO_2)CO_2)$, where $CO_2R(CO_2)CO_2$ is selected from citrate, isocitrate and aconitate; methylamine, ethylamine, propylamine, butylamine, pentylamine, hexylamine, cyclohexylamine, aniline; and $R_4NOH$ where R is selected from methyl, ethyl propyl, butyl. More preferably, the base is selected from one or more of the following: $LiOH$, $NaOH$, $KOH$, $Mg(OH)_2$, $Ca(OH)_2$, $Ba(OH)_2$, $CsOH$, $Sr(OH)_2$, $RbOH$, $NH_4OH$, $Li_2CO_3$, $Na_2CO_3$, $K_2CO_3$, $Rb_2CO_3$, $Cs_2CO_3$, $MgCO_3$, $CaCO_3$, $(NH_4)_2CO_3$, $LiHCO_3$, $NaHCO_3$, $KHCO_3$, $RbHCO_3$, $CsHCO_3$, $Mg(HCO_3)_2$, $Ca(HCO_3)_2$, $Sr(HCO_3)_2$, $Ba(HCO_3)_2$, $NH_4HCO_3$, $Li_2O$, $Na_2O$, $K_2O$, $Rb_2O$, $Cs_2O$, $NH_4(RCO_2)$, $Li(RCO_2)$, $Na(RCO_2)$, $K(RCO_2)$, $Rb(RCO_2)$, $Cs(RCO_2)$, $Mg(RCO_2)_2$, $Ca(RCO_2)_2$, $Sr(RCO_2)_2$ or $Ba(RCO_2)_2$, where $RCO_2$ is selected from itaconate, citrate, oxalate, methacrylate; $(NH_4)_2(CO_2RCO_2)$, $Li_2(CO_2RCO_2)$, $Na_2(CO_2RCO_2)$, $K_2(CO_2RCO_2)$, $Rb_2(CO_2RCO_2)$, $Cs_2(CO_2RCO_2)$, $Mg(CO_2RCO_2)$, $Ca(CO_2RCO_2)$, $Sr(CO_2RCO_2)$, $Ba(CO_2RCO_2)$, $(NH_4)_2(CO_2RCO_2)$, where $CO_2RCO_2$ is selected from malate, fumarate, maleate, citramalate, mesaconate, citraconate, itaconate, oxalate; $(NH_4)_3(CO_2R(CO2)CO_2)$, $Li_3(CO_2R(CO_2)CO_2)$, $Na_3(CO_2R(CO2)CO_2)$, $K_3(CO_2R(CO_2)CO_2)$, $Rb_3(CO_2R(CO_2)CO_2)$, $Cs_3(CO_2R(CO_2)CO_2)$, $Mg_3(CO_2R(CO_2)CO_2)_2$, $Ca_3(CO_2R(CO_2)CO_2)_2$, $Sr_3(CO_2R(CO_2)CO_2)_2$, $Ba_3(CO_2R(CO_2)CO_2)_2$, $(NH_4)_3(CO_2R(CO_2)CO_2)$, where $CO_2R(CO_2)CO_2$ is selected from citrate, isocitrate; tetramethylammonium hydroxide and tetraethylammonium hydroxide. Most preferably, the base is selected from one or more of the following: $NaOH$, $KOH$, $Ca(OH)_2$, $CsOH$, $RbOH$, $NH_4OH$, $Na_2CO_3$, $K_2CO_3$, $Rb_2CO_3$, $Cs_2CO_3$, $MgCO_3$, $CaCO_3$, $(NH_4)_2CO_3$, $NH_4(RCO_2)$, $Na(RCO_2)$, $K(RCO_2)$, $Rb(RCO_2)$, $Cs(RCO_2)$, $Mg(RCO_2)_2$, $Ca(RCO_2)_2$, $Sr(RCO_2)_2$ or $Ba(RCO_2)_2$, where $RCO_2$ is selected from itaconate, citrate, oxalate, methacrylate; $(NH_4)_2(CO_2RCO_2)$, $Na_2(CO_2RCO_2)$, $K_2(CO_2RCO_2)$, $Rb_2(CO_2RCO_2)$, $Cs_2(CO_2RCO_2)$, $Mg(CO_2RCO_2)$, $Ca(CO_2RCO_2)$, $(NH_4)_2(CO_2RCO_2)$, where $CO_2RCO_2$ is selected from citramalate, mesaconate, citraconate, itaconate, oxalate; $(NH_4)_3(CO_2R(CO2)CO_2)$, $Na_3(CO_2R(CO2)CO_2)$, $K_3(CO_2R(CO_2)CO_2)$, $Rb_3(CO_2R(CO_2)CO_2)$, $Cs_3(CO_2R(CO_2)CO_2)$, $Mg_3(CO_2R(CO_2)CO_2)_2$, $Ca_3(CO_2R(CO_2)CO_2)_2$, $(NH_4)_3(CO_2R(CO_2)CO_2)$, where $CO_2R(CO_2)CO_2$ is selected from citrate, isocitrate; and tetramethylammonium hydroxide.

The catalyst may be homogeneous or heterogeneous. In one embodiment, the catalyst may be dissolved in a liquid reaction phase. However, the catalyst may be suspended on a solid support over which the reaction phase may pass. In this scenario, the reaction phase is preferably maintained in a liquid, more preferably, an aqueous phase.

Preferably, the effective mole ratio of base $OH^-$:acid is between 0.001-2:1, more preferably, 0.01-1.2:1, most preferably, 0.1-1:1, especially, 0.3-1:1. By the effective mole ratio of base $OH^-$ is meant the nominal molar content of $OH^-$ derived from the compounds concerned.

By acid is meant the moles of acid. Thus, in the case of a monobasic base, the effective mole ratios of base $OH^-$:acid will coincide with those of the compounds concerned but in the case of di or tribasic bases the effective mole ratio will not coincide with that of mole ratio of the compounds concerned. Specifically, this may be regarded as the mole ratio of monobasic base:di or tri carboxylic acid is preferably between 0.001-2:1, more preferably, 0.01-1.2:1, most preferably, 0.1-1:1, especially, 0.3-1:1.

As the deprotonation of the acid to form the salt is only referring to a first acid deprotonation in the present invention, in the case of di or tribasic bases, the mole ratio of base above will vary accordingly.

Optionally, the methacrylic acid product may be esterified to produce an ester thereof. Potential esters may be selected from $C_1$-$C_{12}$ alkyl or $C_2$-$C_{12}$ hydroxyalkyl, glycidyl, isobornyl, dimethylaminoethyl, tripropyleneglycol esters. Most preferably the alcohols or alkenes used for forming the esters may be derived from bio sources, e.g. biomethanol, bioethanol, biobutanol.

According to a second aspect of the present invention there is provided a method of preparing polymers or copolymers of methacrylic acid or methacrylic acid esters, comprising the steps of
(i) preparation of methacrylic acid in accordance with the first aspect of the present invention;
(ii) optional esterification of the methacrylic acid prepared in (i) to produce the methacrylic acid ester;
(iii) polymerisation of the methacrylic acid prepared in (i) and/or the ester prepared in (ii), optionally with one or more comonomers, to produce polymers or copolymers thereof.

Preferably, the methacrylic acid ester of (ii) above is selected from $C_1$-$C_{12}$ alkyl or $C_2$-$C_{12}$ hydroxyalkyl, glycidyl, isobornyl, dimethylaminoethyl, tripropyleneglycol esters, more preferably, ethyl, n-butyl, i-butyl, hydroxymethyl, hydroxypropyl or methyl methacrylate, most preferably, methyl methacrylate, ethyl acrylate, butyl methacrylate or butyl acrylate.

Advantageously, such polymers will have an appreciable portion if not all of the monomer residues derived from a source other than fossil fuels.

In any case, preferred comonomers include for example, monoethylenically unsaturated carboxylic acids and dicarboxylic acids and their derivatives, such as esters, amides and anhydrides.

Particularly preferred comonomers are acrylic acid, methyl acrylate, ethyl acrylate, propyl acrylate, n-butyl acrylate, iso-butyl acrylate, t-butyl acrylate, 2-ethylhexyl acrylate, hydroxyethyl acrylate, iso-bornyl acrylate, methacrylic acid, methyl methacrylate, ethyl methacrylate, propyl methacrylate, n-butyl methacrylate, iso-butyl methacrylate, t-butyl methacrylate, 2-ethylhexyl methacrylate, hydroxyethyl methacrylate, lauryl methacrylate, glycidyl methacrylate, hydroxypropyl methacrylate, iso-bornyl methacrylate, dimethylaminoethyl methacrylate, tripropyleneglycol diacrylate, styrene, α-methyl styrene, vinyl acetate, isocyanates including toluene diisocyanate and p,p'-methylene diphenyl diisocyanate, acrylonitrile, butadiene, butadiene and styrene (MBS) and ABS subject to any of the above comonomers not being the momomer selected from methacrylic acid or a methacrylic acid ester in (i) or (ii) above in any given copolymerisation of the said acid monomer in (i) or a said ester monomer in (ii) with one or more of the comonomers.

It is of course also possible to use mixtures of different comonomers. The comonomers themselves may or may not be prepared by the same process as the monomers from (i) or (ii) above.

According to a further aspect of the present invention there is provided polyacrylic acid, polymethacrylic acid, polymethylmethacrylate (PMMA) and polybutylmethacrylate homopolymers or copolymers formed from the method of the second aspect of the invention herein.

According to a still further aspect of the present invention there is provided a process for the production of methacrylic acid comprising:—
providing a source of a pre-acid selected from aconitic, citric and/or isocitric acid;
performing a decarboxylation and, if necessary, a dehydration step on the source of pre-acid by exposing the source thereof in the presence or absence of base catalyst to a sufficiently high temperature to provide itaconic, mesaconic and/or citraconic acid; and a process according to the first aspect of the present invention to provide methacrylic acid.

By a source of aconitic, citric and/or isocitric acid is meant the acids and salts thereof such as group I or II metal salts thereof and includes solutions of the pre-acids and salts thereof, such as aqueous solutions thereof.

Optionally, the salt may be acidified to liberate the free acid prior to, during or after the pre-acid decarboxylation step.

Preferably, the dicarboxylic acid(s) reactant(s) are exposed to the reaction conditions for a time period of at least 80 seconds.

Preferably, the dicarboxylic acid(s) reactant(s) or the source of pre-acids thereof of the present invention are exposed to the reaction conditions for a suitable time period to effect the required reaction, such as 80 seconds as defined herein but more preferably, for a time period of at least 100 seconds, yet more preferably at least about 120 seconds and most preferably at least about 150 seconds.

Typically, the dicarboxylic acid(s) reactant(s) or source of pre-acids thereof are exposed to the reaction conditions for a time period of less than about 2000 seconds, more typically less than about 1500 seconds, yet more typically less than about 1000 seconds.

Preferably, the dicarboxylic acid(s) reactant(s) or the source of pre-acids thereof of the present invention are exposed to the reaction conditions for a time period of between about 75 seconds and 2500 seconds, more preferably between about 90 seconds and 1800 seconds and most preferably between about 120 seconds and 800 seconds.

Therefore, according to a further aspect of the present invention there is provided a process for the production of methacrylic acid by the base catalysed decarboxylation of at least one dicarboxylic acid selected from itaconic, citraconic or mesaconic acid or mixtures thereof, wherein the decarboxylation is carried out in the temperature range between 240 and 290° C. and the dicarboxylic acid(s) reactant(s) are exposed to the reaction conditions for a time period of at least 80 seconds.

Advantageously, in this temperature range high selectivities can be achieved at residence times sufficient to allow heating of the reactants in the reaction medium.

Preferably, the dicarboxylic acid(s) reactant(s) or the source of pre-acids thereof of the present invention are dissolved in water so that the reaction occurs under aqueous conditions.

It will be clear from the way in which the above reactions are defined that if the source of pre-acid is decarboxylated and, if necessary, dehydrated in a reaction medium then the reaction medium may simultaneously be effecting base catalysed decarboxylation of the at least one dicarboxylic acid selected from itaconic, citraconic or mesaconic acid or mixtures thereof produced from the source of pre-acid according to the first aspect of the invention. Accordingly, the decarboxylation and if necessary, dehydration of the source of pre-acid and the base catalysed decarboxylation of the at least one dicarboxylic acid may take place in one reaction medium i.e. the two processes may take place as a one pot process. However, it is preferred if the source of pre-acid is decarboxylated and, if necessary, dehydrated substantially without base catalysis so that the decarboxylation and if necessary, dehydration of the source of pre-acid and the base catalysed decarboxylation of the at least one dicarboxylic acid take place in separate steps.

Preferably, the concentration of the dicarboxylic acid reactant(s) is at least 0.1M, preferably in an aqueous source thereof; more preferably at least about 0.2M, preferably in an aqueous source thereof; most preferably at least about 0.3M, preferably in an aqueous source thereof, especially, at least about 0.5M. Generally, the aqueous source is an aqueous solution.

Preferably, the concentration of the dicarboxylic acid reactant(s) is less than about 10M, more preferably, less than 8M, preferably in an aqueous source thereof; more preferably, less than about 5M, preferably in an aqueous source thereof; more preferably less than about 3M, preferably in an aqueous source thereof.

Preferably, the concentration of the dicarboxylic acid reactant(s) is in the range 0.05M-20, typically, 0.05-10M, more preferably, 0.1M-5M, most preferably, 0.3M-3M.

The base catalyst may be dissolvable in a liquid medium, which may be water or the base catalyst may be heterogeneous. The base catalyst may be dissolvable in the reaction mixture so that reaction is effected by exposing the reactants to a temperature in excess of that at which base catalysed decarboxylation of the reactant(s) to methacrylic acid and/or the source of pre-acids to the dicarboxylic acids will occur such as those temperatures given above. The catalyst may be in an aqueous solution.

Accordingly, the catalyst may be homogenous or heterogeneous but is typically homogenous. Preferably, the concentration of the catalyst in the reaction mixture (including the decomposition of the source of pre-acid mixture) is at least 0.1M or greater, preferably in an aqueous source thereof; more preferably at least about 0.2M, preferably in an aqueous source thereof; more preferably at least about 0.3M.

Preferably, the concentration of the catalyst in the reaction mixture (including the decomposition of the source of pre-acid mixture) is less than about 10M, more preferably, less than about 5M, more preferably less than about 2M and, in any case, preferably less than or equal to that which would amount to a saturated solution at the temperature and pressure of the reaction.

Preferably, the mole concentration of $OH^-$ in the aqueous reaction medium or optionally source of pre-acid decomposition is in the range 0.05M-20M, more preferably, 0.1-5M, most preferably, 0.2M-2M.

Preferably, the reaction conditions are weakly acidic. Preferably, the reaction pH is between about 2 and 9, more preferably between about 3 and about 6.

For the avoidance of doubt, by the term itaconic acid, it is meant the following compound of formula (i)

(i)

For the avoidance of doubt, by the term citraconic acid, it is meant the following compound of formula (ii)

(ii)

For the avoidance of doubt, by the term mesaconic acid, it is meant the following compound of formula (iii)

(iii)

As mentioned above, the process of the present invention may be homogenous or heterogeneous. In addition, the process may be a batch or continuous process.

Advantageously, one by-product in the production of MAA may be hydroxy isobutyric acid (HIB) which exists in equilibrium with the product MAA at the conditions used for decomposition of the dicarboxylic acids. Accordingly, partial or total separation of the MAA from the products of the decomposition reaction shifts the equilibrium from HIB to MAA thus generating further MAA during the process or in subsequent processing of the solution after separation of MAA.

As mentioned above, the source of pre-acid such as citric acid, isocitric acid or aconitic acid preferably decomposes under suitable conditions of temperature and pressure and optionally in the presence of base catalyst to one of the dicarboxylic acids of the invention. Suitable conditions for this decomposition are less than 350° C., typically, less than 330° C., more preferably, at up to 310° C., most preferably at up to 300° C. In any case, a preferred lower temperature for the decomposition is 180° C. Preferred temperature ranges for the source of pre-acid decomposition are between 190 and up to 349° C., more preferably, between 200 and 300° C., most preferably, between 210 and 280° C., especially between 220 and 260° C.

Preferably, the source of pre-acid decomposition reaction takes place at a temperature at which the aqueous reaction medium is in the liquid phase.

To maintain the reactants in the liquid phase under the above source of pre-acid decomposition temperature conditions the decarboxylation reaction is carried out at suitable pressures in excess of atmospheric pressure. Suitable pressures which will maintain the reactants in the liquid phase in the above temperature ranges are greater than 150 psi, more suitably, greater than 180 psi, most suitably, greater than 230 psi and in any case at a higher pressure than that below which the reactant medium will boil. There is no upper limit of pressure but the skilled person will operate within practical limits and within apparatus tolerances, for instance, at less than 10,000 psi, more typically, at less than 5,000 psi, most typically, at less than 4000 psi.

Preferably, the source of pre-acid decomposition reaction is at a pressure of between about 150 and 10000 psi. More preferably, the reaction is at a pressure of between about 180 and 5000 psi and yet more preferably between about 230 and 3000 psi.

In a preferred embodiment, the source of pre-acid decomposition reaction is at a pressure at which the reaction medium is in the liquid phase.

Preferably, the source of pre-acid decomposition reaction is at a temperature and pressure at which the aqueous reaction medium is in the liquid phase.

All of the features contained herein may be combined with any of the above aspects, in any combination.

For a better understanding of the invention, and to show how embodiments of the same may be carried into effect, reference will now be made, by way of example, to the following figures and examples.

EXAMPLES

A series of experiments were conducted investigating the decomposition of itaconic, citraconic and mesaconic acids to form methacrylic acid at various temperatures and residence times. The procedure for these experiments is as follows.

General Procedure

A reactant feed solution was prepared comprising itaconic, citraconic or mesaconic acid at a concentration of 0.5 M and sodium hydroxide also at a concentration of 0.5 M. The itaconic acid used (>=99%) was obtained from Sigma Aldrich (Catalogue number: L2, 920-4); citraconic acid (98+%) was obtained from Alfa Aesar (L044178); mesaconic acid (99%) was obtained from Sigma Aldrich (Catalogue number: 13, 104-0). The deionised water used for solvation of the precursor acids/NaOH was first degassed via sonication in an Ultrasound Bath (30 Khz) for a period of 5 minutes.

This reactant feed solution was fed into the reactor system via a Gilson 305 HPLC pump module fitted with a Gilson 10 SC pump head. The rate at which the reactant feed solution was pumped into the reactor system depended on the residence time required and the volume of the reactor. The feed rate was also dependent on the density of the reaction media which in turn depended on the reaction temperature.

The reactant feed solution was pumped to the reactor via 1/16" internal diameter stainless steel (SS 316) pipe (Sandvik). The reactor consisted of a straight section of 1/2" SS 316 pipe, encased in an aluminium block fitted with two 800W Watlow heater cartridges. The transition of the SS 316 piping from 1/16" to 1/2" was achieved with Swagelok SS 316 reducing unions and required an intermediate step of 1/8" pipe (i.e. 1/16" pipe to 1/8" pipe to 1/2" pipe).

The volume of the reactor was calculated theoretically, and confirmed from the difference in weight when the reactor was filled with water and when it was dry; for the experiments described, the volume of the reactor was 19.4 cm$^3$. After the 1/2" pipe 'reactor', the piping was reduced back down to 1/16", before meeting a Swagelok SS 316 1/16" cross-piece. At this cross-piece, a thermocouple (type K) was used to monitor the temperature of the exit feed.

Reactor volume (used for residence time) is defined as the volume of the 1/2" section of pipe between the two 1/2" to 1/8" reducers located immediately before and after the aluminium block.

The product mixture is finally passed through a heat exchanger (a length of 1/8" pipe within a 1/4" pipe through which cold water was passed in contra flow) and a manual Tescom Back-Pressure Regulator through which back-pressure (pressure throughout the whole system between this point and the pump head) was generated: the pressure employed was 3000 psi for all experiments described. Samples were collected in vials before being prepared for analysis.

The required temperature for reaction was achieved using a thermostat fitted with a Gefran controller (800 P), which mediated power applied to the two Watlow cartridge heaters. Each set of experiments involved working at a single temperature while varying residence time between runs. The required flow rate for the first run was set at the Gilson pump module. The pump was then left for a period of around 20 minutes, pumping only deionised water, in order for the heat-transfer between the aluminium block to have become consistent. The heat-transfer was deemed to have achieved equilibrium when the temperature indicated by the thermocouple located at the reactor exit feed position did not change (accurate to 1° C.) for a period of more than 5 minutes. At this stage the inlet of the pump was transferred from the container of deionised water to the container of the prepared reactant mixture. The total volume of the apparatus (including reactor) was approximately double that of the reactor itself; this was previously determined experimentally. For a particular flow rate, the reactant mixture was left pumping for approximately three times the required period for it to have begun emerging from the final outlet, in order to ensure that a steady-state of reaction had been achieved. After this time a 20 ml sample of the apparatus exit solution was collected for analysis. Both the rate of collection of the exit solution and the rate at which the precursor solution was consumed were recorded against time in order to monitor the consistency of the pump efficiency. Following sample collection from a particular run, the pump inlet was switched back to the container of deionised water, and the flow rate was increased to its maximum for a period of approximately 10 minutes to ensure that all remaining material from the previous run had been purged from the system. This procedure was then repeated for the subsequent residence time to be investigated.

Analysis

Quantitative analysis of products was achieved using an Agilent 1200 series HPLC system equipped with a multi wave-length UV detector. Products were separated using a Phenomenex Rezex RHM monosaccharide H$^+$ (8%) column held at 75° C., protected by a guard column. The method used was isocratic, implementing a 0.4 mlmin$^{-1}$ flow rate of aqueous 0.005 M H$_2$SO$_4$ mobile phase. The compounds contained in product samples were found to have optimum UV absorbance at the shortest wavelength capable of the MWD detector of 210 nm (bandwidth 15 nm). All product compounds were calibrated for their UV detection, by correlating their UV absorbance against a range of concentrations. Linear response ranges were determined for each compound, and the most compatible range of concentrations found for all compounds of interest was between $5\times10^{-3}$ M and $1\times10^{-3}$ M. Thus, adequate quantitative detection of most products was achieved with a 1 to 100 dilution of samples obtained from the apparatus before HPLC analysis (a dilution of 1 to 100 would mean that when starting with a 0.5 M precursor solution, any product generated in a yield of between 20%-100% would fall within the linear response range of concentrations). Where compounds fell outside this linear response range (e.g. a yield of less than 20%), a second HPLC analysis was conducted using a dilution of 1 to 10. Any samples which were not accurately quantified using the 1 to 10 dilution method were considered to be trace in concentration and therefore negligible.

Procedure

Figure 1:
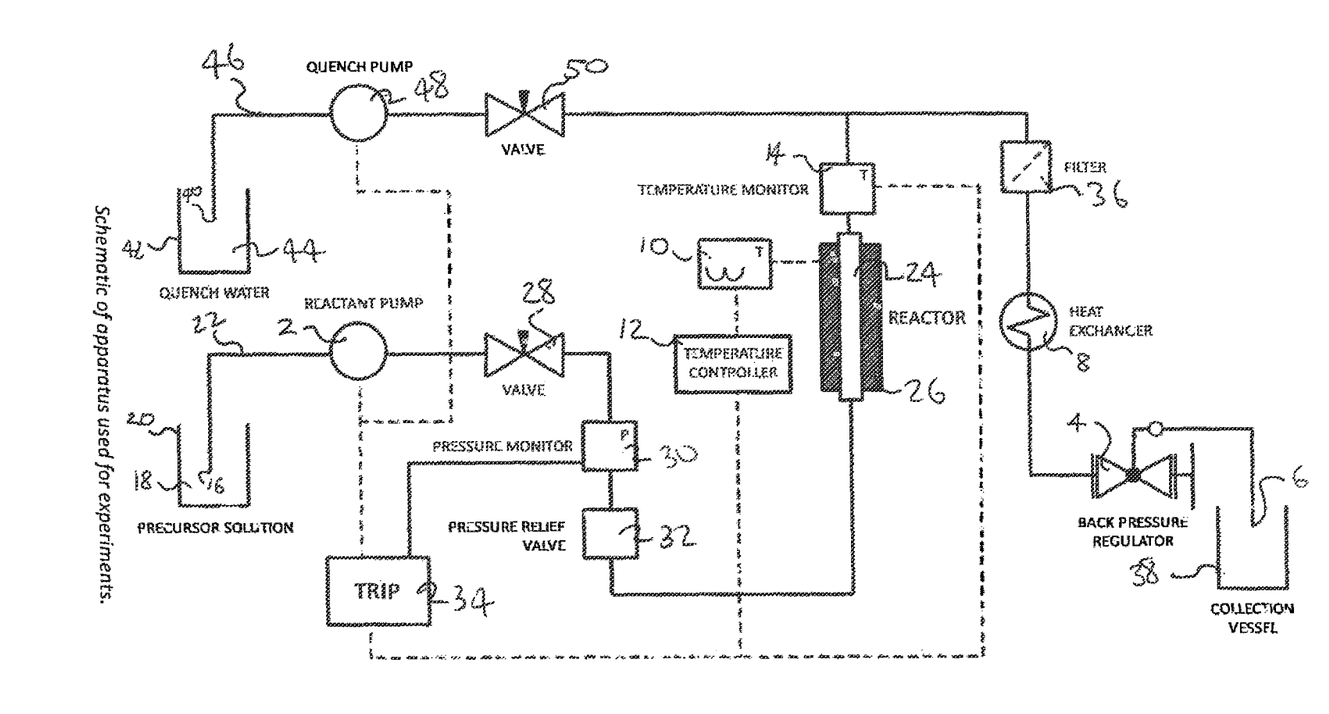
FIG. 1 shows a schematic of apparatus used for the examples of the invention.

The following procedure was carried out. The reagent mixture comprising acid precursor and sodium hydroxide was first prepared. The required flow rate to achieve the residence time was calculated using the reactor volume and the density of water (calculated from temperature). FIG. 1 shows a schematic representation of the apparatus for the present invention. Precursor solution 18 was located in receptacle 20 which was connected to inlet 16. The inlet was connected via conduit 22 to the reactant pump 2 which was operable to pump the solution 18 to the reactor tube 24 tube which was housed in a heater cartridge 26 which extended circumferentially along the reactor 24 length. The conduit 22 between the pump 2 and the reactor 24 proceeded from the pump via a valve 28 for operation control, pressure monitor 30 and pressure relief valve 32. In addition, a trip switch 34 was connected to the pressure monitor 30, reactant pump 2 and a temperature monitor 14. The temperature monitor 14 was located in conduit 22 immediately after reactor 24 and before outlet 6. In addition, after the monitor 14, the conduit proceeded to the outlet via a filter 36, heat exchanger 8 and back pressure regulator 4. At the outlet 6, the product was collected in collection receptacle 38.

The reactor 24 also included a temperature control unit 10, 12 to control the temperature of the reactor 24. The apparatus also included a quenching system which includes a separate inlet 40 for quench water 44 in quench water receptacle 42. The inlet 40 was connected to the outlet 6 via conduit 46 which included a separate quench pump 48 followed by a valve 50 for control of the quench water. The quench water conduit 46 met the reaction conduit 22 immediately after the temperature monitor 14 of the reactor 24 and before filter 36 to quench any reaction after the reactor. The quench pump 48 and temperature controller unit 10, 12 were also connected to trip switch 34 for necessary shut down when the trip criteria are met.

The reactor pump 2 was turned on and deionised water was pumped into the system. The back pressure regulator 4 was gradually adjusted to the required pressure (3000 psi).

The pump operation efficiency was checked at 5 ml min$^{-1}$ by recording time taken to collect a volume of 20 ml of water from system outlet 6. >90% efficiency was acceptable.

The pump flow rate is then set to that required for the run.

The water supply (not shown) to the heat exchanger 8 was set to a low-moderate flow, depending on the reaction temperature and pump flow rate for the experiment.

The heater thermostat 10 fitted with a temperature controller 12 was set to the required temperature for the run.

Once the required temperature had been reached (as indicated by thermostat 10), reactor outlet temperature was monitored by the reactor temperature monitor 14 until the value (accurate to 1° C.) was observed to remain static for a period of at least 5 minutes (this usually took approximately 20 minutes).

The pump inlet 16 was switched from the deionised water container (not shown) to the prepared reagent mixture container 18 (this requires stopping the pump flow for a few seconds). The initial volume of reagent mixture in container 18 was recorded.

Calculations can indicate the period before product solution will begin to emerge from the system outlet 6. However, in practice, this was confirmed by the visual and audible presence of gas bubbles exiting the apparatus (generated from the decomposition of reagents). This was allowed to continue for a period that is ×3 the period taken for the product solution to emerge. This ensured that the product mixture is homogenous.

At the outlet 6, 20 ml of product solution was collected and the time taken for this collection was recorded. A final time and volume reading was also taken for the reagent mixture.

After product collection, the pump inlet was transferred back to the deionised water container, and the pump was set to "prime mode" (maximum flow rate) and left for a period of approximately 10 minutes.

The flow rate of the pump was then set to the required value for the subsequent run.

Again the reactor outlet temperature was monitored and was considered steady when the value did not change for a period of at least 5 minutes (this usually took approximately 10 minutes).

This experimental method was repeated until all required runs for the experiment had been performed. After all runs had been completed, the deionised water was pumped into the system with the pump on prime mode and the heater (thermostat) was switched off.

When the reactor outlet temperature had dropped below 80° C., the pump was switched off and the water supply to the heat exchanger was also ceased.

Product yields are expressed as absolute mole percent (100×moles product/mole of reactant fed)

Example 1

Itaconic Acid Decomposition

| Precursor | | | | 0.5M Itaconic Acid | | | |
|---|---|---|---|---|---|---|---|
| Base | | | | NaOH | | | |
| Base Conc. | | | | 0.5M | | | |
| Temp | | | | 250° C. | | | |
| Pressure | | | | 3000 psi | | | |
| Residence Time (seconds) | MAA Yield | PY Yield | CC Yield | IC Yield | HIB/PC Yield | MC Yield | CT Yield |
| 540 | 19.25 | 0.36 | 36.76 | 16.35 | 11.26 | 15.18 | 0.07 |

Selectivity = Yield MAA/(1-(Yield IC + Yield CC + Yield MC + Yield HIB/PC))
Selectivity = 94.13%

Where
- MAA Methacrylic acid
- PY pyruvic acid
- CC citraconic acid
- CM citramalic acid
- IC itaconic acid
- HIB hydroxyisobutyric acid
- MC mesaconic acid
- CT crotonic acid
- PC paraconic

Comparative Example 1

Itaconic Acid Decomposition

| Precursor | | | | 0.5M Itaconic Acid | | |
|---|---|---|---|---|---|---|
| Base | | | | NaOH | | |
| Base Conc. | | | | 0.5M | | |
| Temp | | | | 310° C. | | |
| Pressure | | | | 3000 psi | | |

| Residence Time | MAA Yield | PY Yield | CC Yield | IC Yield | HIB/PC Yield | MC Yield | CT Yield |
|---|---|---|---|---|---|---|---|
| 540 | 58.36 | 2.69 | 0.50 | 0.84 | 22.12 | 0.64 | 0.74 |

Selectivity = Yield MAA/(1-(Yield IC + Yield CC + Yield MC + Yield HIB/PC))
Selectivity = 76.89%

Comparative Example 2

Itaconic Acid Decomposition

| Precursor | | | | 0.5M Itaconic Acid | | |
|---|---|---|---|---|---|---|
| Base | | | | NaOH | | |
| Base Conc. | | | | 0.5M | | |
| Temp | | | | 330° C. | | |
| Pressure | | | | 3000 psi | | |

| Residence Time | MAA Yield | PY Yield | CC Yield | IC Yield | HIB/PC Yield | MC Yield | CT Yield |
|---|---|---|---|---|---|---|---|
| 480 | 56.74 | 2.63 | 0 | 0 | 19.33 | 0.08 | 0.53 |

Selectivity = Yield MAA/(1-(Yield IC + Yield CC + Yield MC + Yield HIB/PC))
Selectivity = 70.41%

Comparative Example 3

Itaconic Acid Decomposition

| Precursor | | | | 0.5M Itaconic Acid | | |
|---|---|---|---|---|---|---|
| Base | | | | NaOH | | |
| Base Conc. | | | | 0.5M | | |
| Temp | | | | 350° C. | | |
| Pressure | | | | 3000 psi | | |

| Residence Time | MAA Yield | PY Yield | CC Yield | IC Yield | HIB/PC Yield | MC Yield | CT Yield |
|---|---|---|---|---|---|---|---|
| 180 | 54.42 | 2.67 | 0.26 | 0.16 | 13.07 | 0.30 | 0.63 |

Selectivity = Yield MAA/(1-(Yield IC + Yield CC + Yield MC + Yield HIB/PC))
Selectivity = 63.12%

Example 2-12 and Comparative Examples 4-9

General Procedure

A reactant feed solution was prepared comprising itaconic, citraconic or mesaconic acid at a concentration of 0.5 M and sodium hydroxide at a concentration of 0.5 M. The itaconic acid used (>=99%) was obtained from Sigma Aldrich (Catalogue number: L2, 920-4); citraconic acid (98+%) was obtained from Alfa Aesar (L044178); mesaconic acid (99%) was obtained from Sigma Aldrich (Catalogue number: 13, 104-0).

This reactant feed solution was fed into the reactor system via a Gilson 205 HPLC pump module fitted with a 10 SC pump head. The flow rate of the pump was controlled from a computer running Gilson Unipoint software. The reactant feed solution was pumped to the reactor via 1/16" internal diameter stainless steel (SS 316) pipe (Sandvik). The reactor consisted of a length of 1/18" SS 316 pipe coil around a cylindrical aluminium former, the orbiting surface of which had been threaded to the dimensions of the 1/8" pipe, ensuring high contact area between the former and the pipe. This cylindrical former had a 1 kW Watlow heater cartridge at its core, providing heat via conduction from the centre of the former. The outside of the pipe coil was also encased within a 1 kW Watlow cuff heater. A spacer layer fabricated from brass was situated between the cuff heater and the outer face of the pipe coil, with threading on the inside surface (contacting the pipe), in order to ensure good surface area contact and thus heat transfer from the cuff heater to the pipe. The 1/8" pipe used for the reactor was fitted with Swagelok 1/16" to 1/18" ss 316 reducing unions at either end thereof. The reducing union at the reactor outlet immediately preceded union to a Swagelok ss 316 1/16" cross piece, which introduced a second feed of quenching water, allowed for temperature measurements with a type K 1/16" thermocouple (Radio Spares), and provided an exit route for the quenched product stream. The entire reactor system including the reducing union components, up until the 1/16" cross-piece, was thermally insulated with layers of glass wool, aluminium foil and glass wool woven tape; this acted to minimise temperature gradients at the reactor inlet and at the reactor outlet, between the heater itself and the 1/16" cross-piece.

Two reactor volumes were used for investigating different ranges of residence times, and the volume was adjusted by reducing the number of coils around the aluminium former of the reactor. The volume of the reactor in each case was considered to be between the reducing union at the reactor inlet, and the quenching point at the 1/16"cross-piece at the reactor outlet. In both cases the assumed reactor volume was determined by pumping an accurately measured quantity of water into the empty reactor components, which had been previously dried at elevated temperature followed by purging with nitrogen gas; this process was repeated several times in case of discrepancy.

After quenching, the product mixture was finally passed through a heat exchanger, consisting of an approximately 1.5 m length of the 1/16" pipe following the quenching point passing through 1/4" ss 316 pipe of the of the same length, through which water could be directed in contra flow, in order to remove residual heat from the product mixture stream; the pipe dimensions for this heat exchanger system were selected in order to minimise the total volume of the apparatus. The product stream was finally passed through a manual Tescom back-pressure regulator through which back-pressure (pressure throughout the whole system between this point and the pump head) was generated: the pressure employed was 3000 psi for all experiments described.

Samples from each investigated residence time were collected in vials automatically using Gilson 201 fraction collector, which was also controlled from the Unipoint software. The programmes scripted in Unipoint operated using the following protocol: The flow rate would adjust to that required for a specific residence time, as previously calculated; the pump would then remain pumping at this flow rate until a volume equal to three times that of the entire apparatus has been passed through the system, allowing adequate time for both the heater and composition of the product stream to equilibrate; the fraction collector would then move the flow system outlet to a designated fraction site and collect an instructed volume of the aqueous product; the fraction collector would finally move the flow system outlet to a waste receptacle, and the flow rate at the pump would be adjusted to that required for the next residence time of interest.

The required temperature for each experiment was achieved using a thermostat fitted with a Gefran controller (800 P), which mediated power applied to both the Watlow cartridge heater and Watlow cuff heater. The achieved temperature was monitored by the thermostat via a 1/16" type K thermocouple sited in a 1/16" cavity which has been drilled into the top of the aluminium former, close to the contact point with the pipe coil. A second thermocouple was located in a second cavity in close proximity to the first, which monitored the temperature on an independent temperature display module; this module was connected to an electronic trip circuit which was able to cut power to all electronic devices in the case of over-temperature and was also used to check for consistency between its recorded temperature and that measured by the thermostat. For each experiment, the thermostat was tuned to the required temperature, whilst being subjected to the greatest flow rate that would be required, i.e. where maximum power would be required by the heater. Tuning the thermostat in this way evidenced the minimum time required for equilibration of power supplied to the heater where the flow rate was sequentially reduced if longer residence times were investigated in each experiment. In the case of all residence time investigations, as the flow rate was initially altered, the reactor was seen to adjust to the set-temperature (accurate to 1° C.) within a negligible fraction of the total time allowed for equilibration.

Throughout these experiments, the quench flow was universally set to equal that of the precursor flow through the reactor; this allowed for a substantially consistent degree of quenching as the precursor flow rate, and hence residence time, was varied. Immediately prior to the initiation of power to the thermostat (and thus reactor heaters), precursor samples were collected at the different flow rates required during the experiments, accompanied by the quench flow equal to that of the precursor flow in each case. These precursor samples would be compared to that of the product samples during the analysis in order to determine product yields and mass balances. Collecting the precursor samples in this way aids to account for flow-rate efficiency variations between the two pumps at the different flow rates of interest.

Analysis

Quantitative analysis of the majority of products was achieved using an Agilent 1200 series HPLC system equipped with a multi wave-length UV detector. Products were separated using a Phenomenex Rezex RHM monosaccharide H' (8%) column held at 75° C., protected by a guard column. The method used was isocratic, implementing a 0.4 mlmin$^{-1}$ flow rate of aqueous 0.005 M $H_2SO_4$ mobile phase. The compounds contained in product samples were found to have optimum UV absorbance at the shortest wavelength capable of the MWD detector of 210 nm (bandwidth 15 nm). All product compounds were calibrated for their UV detection, by correlating their UV absorbance against a range of concentrations. Linear response ranges were determined for each compound, and the most compatible range of concentrations found for all compounds of interest was between $5 \times 10^{-3}$ M and $1 \times 10^{-3}$ M. Thus, adequate quantitative detection of most products was achieved with a 1 to 100 dilution of samples obtained from the apparatus before HPLC analysis (a dilution of 1 to 100 would mean that when starting with a 0.5 M precursor solution, any product generated in a yield of between 20%-100% would fall within the linear response range of concentrations). Where compounds fell outside this linear response range (e.g. a yield of less than 20%), a second HPLC analysis was conducted using a dilution of 1 to 10. Compounds which were not accurately quantified using the 1 to 10 dilution method were considered to be trace in concentration and therefore negligible.

A limited number of product components could not be quantified via HPLC with UV detection, either due to their poor UV absorbance, or due to co-elution issues during chromatographic separation. These components were instead quantified by $^1$H NMR, using a Bruker dpx 300 Mhz NMR system. The product samples were analysed in aqueous form as produced by the apparatus (giving a sum product concentration of approximately 0.25 M after dilution by the quenching stream), diluted in $D_2O$ (Aldrich, 99.98%) in a ratio of 1:2 respectively. No internal standard was added, and the concentrations of the various species were instead standardised against a well resolved resonance peak of a component whose concentration was accurately know from the HPLC analysis. For this purpose, either the proton resonance peak for the non-terminal $CH_2$ feature of itaconic acid, $\delta$ 3.18 ppm (equivalent to 2 protons), or the terminal methyl $CH_3$ feature of methacrylic acid, $\delta$ 1.79 ppm (equivalent to 3 protons), was selected dependent on which was larger. Integrals of all other resonance peaks in the spectrum could be used to quantify all other chemical species in the product mixture based on the concentration of itaconic or methacrylic acid as previously determined by UV detection; however, where quantification of components was available from both UV and NMR detection, the UV detection (via HPLC) was selected in preference due to increased accuracy; the comparison of the NMR and UV quantifications were compared however, and used to assess continuity and reliability between the two analytical techniques, and ultimately evaluate the accuracy of the quantification of products which could be determined solely from NMR analysis. The products which were quantified exclusively by means of NMR analysis were as follows: Acetone, for which the resonance peak at $\delta$ 2.13 ppm, equivalent to 6 protons was used; hydroxyisobutyric acid, for which the resonance peak at $\delta$ 1.27 ppm, equivalent to 6 protons was used; paraconic acid, for which the resonance peak at $\delta$ 3.29 ppm, equivalent to a single proton was used.

The formation and decomposition of crotonic acid to propene was modelled from the empirical data to give a quantitative estimate of propene. An estimate of propene was also carried out using micro GC to check the validity of the model.

A series of decarboxylation experiments were carried out on itaconic (IC), citraconic (CC) and mesaconic (MC) acid at various temperatures and residence times according to the above procedure. The results are shown below.

TABLE 1

Yield and Selectivity at Various Temperatures

| Example | Res time/s | Temp °C. | Mol % Yield Pyruvic | CC | Citramalic | IC | HIB | MC | MAA | Crotonic | Paraconic | Propene | Selectivity |
|---|---|---|---|---|---|---|---|---|---|---|---|---|---|
| 2(IC) | 160 | 245 | 0.00 | 41.40 | 0.00 | 15.55 | 1.70 | 15.48 | 16.15 | 0.05 | 9.62 | 0.05 | 99.38 |
| 3(CC) | 140 | 250 | 0.39 | 39.85 | 0.00 | 15.44 | 1.38 | 17.61 | 16.18 | 0.02 | 9.02 | 0.11 | 96.88 |
| 4(IC) | 90 | 250 | 0.21 | 44.33 | 0.00 | 16.20 | 1.01 | 13.99 | 14.30 | 0.00 | 9.91 | 0.06 | 98.21 |
| 5(IC) | 300 | 250 | 1.26 | 28.11 | 0.00 | 10.88 | 5.36 | 16.76 | 29.72 | 0.00 | 7.30 | 0.61 | 94.08 |
| 6(MC) | 140 | 250 | 0.16 | 45.82 | 0.00 | 16.93 | 1.10 | 13.42 | 11.63 | 0.00 | 10.94 | 0.10 | 98.64 |
| 7(IC) | 90 | 260 | 0.48 | 36.39 | 0.00 | 13.35 | 2.23 | 15.98 | 22.36 | 0.20 | 8.17 | 0.85 | 93.62 |
| 8((CC) | 80 | 260 | 0.86 | 38.11 | 0.00 | 14.50 | 1.72 | 16.21 | 20.64 | 0.25 | 7.27 | 0.44 | 93.01 |
| 9(MC) | 80 | 260 | 0.33 | 29.53 | 0.00 | 11.27 | 0.48 | 46.37 | 8.12 | 0.00 | 3.70 | 0.12 | 93.71 |
| 10(IC) | 90 | 270 | 0.96 | 28.57 | 0.00 | 10.69 | 4.12 | 16.10 | 32.23 | 0.32 | 5.25 | 1.76 | 91.37 |
| 11((CC) | 80 | 270 | 1.47 | 29.37 | 0.00 | 11.51 | 4.28 | 16.45 | 31.67 | 0.63 | 3.72 | 0.89 | 91.35 |
| 12(MC) | 80 | 270 | 0.98 | 30.27 | 0.00 | 11.34 | 1.6 | 36.77 | 16.39 | 0.33 | 2.01 | 0.31 | 91.01 |
| Comp 4(IC) | 210 | 280 | 4.01 | 5.91 | 0.00 | 2.60 | 17.55 | 5.72 | 57.08 | 1.01 | 1.22 | 4.91 | 85.19 |
| Comp 5(CC) | 200 | 280 | 1.39 | 14.92 | 0.00 | 5.63 | 10.37 | 9.78 | 46.79 | 0.71 | 2.64 | 7.78 | 82.58 |
| Comp 6 (MC) | 200 | 280 | 1.21 | 18.79 | 0.00 | 7.09 | 8.18 | 12.49 | 42.74 | 0.64 | 3.29 | 5.57 | 85.21 |
| Comp 7(IC) | 150 | 300 | 4.14 | 1.47 | 0.00 | 0.72 | 20.27 | 1.68 | 63.13 | 1.05 | 1.17 | 6.31 | 84.53 |
| Comp 8(CC) | 200 | 300 | 3.02 | 2.86 | 0.00 | 1.00 | 15.66 | 1.72 | 55.85 | 1.14 | 2.92 | 16.03 | 73.44 |
| Comp 9(MC) | 200 | 300 | 2.96 | 3.55 | 0.00 | 1.33 | 15.2 | 2.29 | 56.42 | 1.15 | 2.86 | 14.24 | 75.46 |

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A continuous process for the production of methacrylic acid by the base catalysed decarboxylation of at least one dicarboxylic acid selected from itaconic, citraconic or mesaconic acid or mixtures thereof, followed by separation of the methacrylic acid product, wherein the decarboxylation is carried out at greater than 240 and up to 275° C. and at pressures which will maintain the reactants in the liquid phase.

2. A process according to claim 1, wherein the decarboxylation is in the temperature range between 245 and up to 275° C.

3. A process according to claim 1, wherein the dicarboxylic acid reactants are in aqueous solution.

4. A process according to claim 1, wherein the decarboxylation reaction is carried out at suitable pressures in excess of atmospheric pressure.

5. A process according to claim 1, wherein the base catalyst comprises a metal oxide, hydroxide, carbonate, acetate (ethanoate), alkoxide, hydrogencarbonate or salt of a decomposable di- or tri-carboxylic acid, or a quaternary ammonium hydroxide, carbonate, acetate (ethanoate), alkoxide or hydrogencarbonate, or one or more amines.

6. A process according to claim 1, wherein the base catalyst is selected from one or more of the following: LiOH, NaOH, KOH, $Mg(OH)_2$, $Ca(OH)_2$, $Ba(OH)_2$, CsOH, $Sr(OH)_2$, RbOH, $NH_4OH$, $Li_2CO_3$, $Na_2CO_3$, $K_2CO_3$, $Rb_2CO_3$, $Cs_2CO_3$, $MgCO_3$, $CaCO_3$, $SrCO_3$, $BaCO_3$, $(NH_4)_2CO_3$, $LiHCO_3$, $NaHCO_3$, $KHCO_3$, $RbHCO_3$, $CsHCO_3$, $Mg(HCO_3)_2$, $Ca(HCO_3)_2$, $Sr(HCO_3)_2$, $Ba(HCO_3)_2$, $NH_4HCO_3$, $Li_2O$, $Na_2O$, $K_2O$, $Rb_2O$, $Cs_2O$, MgO, CaO, SrO, BaO, $Li(OR^1)$, $Na(OR^1)$, $K(OR^1)$, $Rb(OR^1)$, $Cs(OR^1)$, $Mg(OR^1)_2$, $Ca(OR^1)_2$, $Sr(OR^1)_2$, $Ba(OR^1)_2$, $NH_4(OR^1)$ where $R^1$ is any $C_1$ to $C_6$ branched, unbranched or cyclic alkyl group, being optionally substituted with one or more functional groups; $NH_4(RCO_2)$, $Li(RCO_2)$, $Na(RCO_2)$, $K(RCO_2)$, $Rb(RCO_2)$, $Cs(RCO_2)$, $Mg(RCO_2)_2$, $Ca(RCO_2)_2$, $Sr(RCO_2)_2$ or $Ba(RCO_2)_2$, where $RCO_2$ is selected from citramalate, mesaconate, citraconate, itaconate, citrate, oxalate and methacrylate; $(NH_4)_2(CO_2RCO_2)$, $Li_2(CO_2RCO_2)$, $Na_2(CO_2RCO_2)$, $K_2(CO_2RCO_2)$, $Rb_2(CO_2RCO_2)$, $Cs_2(CO_2RCO_2)$, $Mg(CO_2RCO_2)$, $Ca(CO_2RCO_2)$, $Sr(CO_2RCO_2)$, $Ba(CO_2RCO_2)$, $(NH_4)_2(CO_2RCO_2)$, where $CO_2RCO_2$ is selected from citramalate, mesaconate, citraconate, itaconate and oxalate; $(NH_4)_3(CO_2R(CO2)CO_2)$, $Li_3(CO_2R(CO_2)CO_2)$, $Na_3(CO_2R(CO2)CO_2)$, $K_3(CO_2R(CO_2)CO_2)$, $Rb_3(CO_2R(CO_2)CO_2)$, $Cs_3(CO_2R(CO_2)CO_2)$, $Mg_3(CO_2R(CO_2)CO_2)_2$, $Ca_3(CO_2R(CO_2)CO_2)_2$, $Sr_3(CO_2R(CO_2)CO_2)_2$, $Ba_3(CO_2R(CO_2)CO_2)_2$, $(NH_4)_3(CO_2R(CO_2)CO_2)$, where $CO_2R(CO_2)CO_2$ is selected from citrate, isocitrate and aconitate; methylamine, ethylamine, propylamine, butylamine, pentylamine, hexylamine, cyclohexylamine, and aniline; and $R_4NOH$ where R is selected from methyl, ethyl propyl, butyl.

7. A process according to claim 1, wherein the catalyst may be homogeneous or heterogeneous.

8. A process according to claim 1, wherein the effective mole ratio of base $OH^-$:acid is between 0.001:1 and -2:1.

9. A process according to claim 1, wherein the methacrylic acid product is esterified to produce an ester thereof.

10. A process according to claim 1, wherein the concentration of the dicarboxylic acid reactant(s) is at least 0.1M.

11. A process according to claim 1, wherein the concentration of the catalyst in the reaction mixture is at least 0.1M.

12. A continuous process for the production of methacrylic acid by the base catalysed decarboxylation of at least one dicarboxylic acid selected from itaconic, citraconic or mesaconic acid or mixtures thereof followed by separation of the methacrylic acid product, wherein the decarboxylation is carried out in the temperature range between 240 and 290° C. and the dicarboxylic acid(s) reactant(s) are exposed to the reaction conditions for a time period of at least 80 seconds and at pressures which will maintain the reactants in the liquid phase.

13. A process according to claim 1, wherein the dicarboxylic acid reactants and the base catalyst are in aqueous solution.

* * * * *